(12) United States Patent
Ohta (10) Patent No.: US 8,050,383 B2
(45) Date of Patent: Nov. 1, 2011

(54) RADIOGRAPHIC APPARATUS AND RADIOGRAPHIC METHOD

(75) Inventor: Yasunori Ohta, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 135 days.

(21) Appl. No.: 12/545,891

(22) Filed: Aug. 24, 2009

(65) Prior Publication Data

US 2010/0054398 A1    Mar. 4, 2010

(30) Foreign Application Priority Data

Sep. 2, 2008  (JP) ................. 2008-225209

(51) Int. Cl.
  *G01N 23/083*  (2006.01)
  *H05G 1/42*  (2006.01)
(52) U.S. Cl. .......................... 378/62; 378/97
(58) Field of Classification Search .............. 378/62, 378/97, 108, 145, 150, 151, 152, 205, 206, 378/207
See application file for complete search history.

(56) References Cited

U.S. PATENT DOCUMENTS

| | | | |
|---|---|---|---|
| 3,581,094 A | 5/1971 | Peyser et al. | |
| 3,947,689 A | 3/1976 | Wagner | |
| 6,106,152 A * | 8/2000 | Thunberg | 378/205 |
| 6,259,767 B1 * | 7/2001 | Neumann et al. | 378/151 |
| 6,292,537 B1 * | 9/2001 | Zimmermann | 378/108 |
| 6,375,354 B1 * | 4/2002 | Polkus et al. | 378/205 |
| 6,402,373 B1 * | 6/2002 | Polkus et al. | 378/207 |
| 6,422,749 B1 * | 7/2002 | Polkus et al. | 378/205 |
| 6,435,716 B1 * | 8/2002 | Polkus et al. | 378/205 |
| 6,447,164 B1 * | 9/2002 | Polkus | 378/206 |
| 6,478,462 B2 * | 11/2002 | Polkus et al. | 378/207 |
| 6,647,092 B2 * | 11/2003 | Eberhard et al. | 378/65 |
| 7,003,145 B2 * | 2/2006 | Polkus et al. | 382/132 |
| 7,110,495 B2 * | 9/2006 | Tamegai | 378/97 |
| 2002/0122534 A1 | 9/2002 | Polkus et al. | |
| 2006/0291614 A1 | 12/2006 | Horiuchi et al. | |
| 2010/0266098 A1 * | 10/2010 | Takasaki | 378/62 |

FOREIGN PATENT DOCUMENTS

| | | |
|---|---|---|
| EP | 0121151 A1 | 10/1984 |
| EP | 1388741 A2 | 2/2004 |
| JP | 2002-204794 | 7/2002 |
| JP | 2004-201757 | 7/2004 |
| JP | 2005-198975 | 7/2005 |
| JP | 2007-181686 | 7/2007 |

OTHER PUBLICATIONS

Corresponding EPO Official Communication.

* cited by examiner

*Primary Examiner* — Allen C. Ho
(74) *Attorney, Agent, or Firm* — SOLARIS Intellectual Property Group, PLLC (57) ABSTRACT

A radiographic apparatus controls the irradiation of a subject with radiation on the basis of a comparison result between an irradiation area calculated on the basis of an opening area of an aperture and a detection area of radiation of an image data generator that detects radiation that has been transmitted through the subject and generates image data.

9 Claims, 4 Drawing Sheets

RADIOGRAPHIC APPARATUS AND RADIOGRAPHIC METHOD

CROSS-REFERENCE TO RELATED APPLICATIONS

This application claims priority under 35 USC 119 from Japanese Patent Application No. 2008-225209 filed on Sep. 2, 2008, the disclosure of which is incorporated by reference herein.

BACKGROUND OF THE INVENTION

1. Field of the Invention

The present invention relates to a radiographic apparatus and a radiographic method.

2. Description of the Related Art

In recent years, flat panel detectors (FPD) that comprise an X-ray sensitive layer disposed on a thin-film transistor (TFT) active matrix substrate and can directly convert X rays into digital data have been put to practical use. Portable radiographic image detection devices (called "electronic cassettes" below) that use an FPD or the like to generate image data, which represent a radiographic image expressed by radiation that has been transmitted through a subject such as an examinee and with which the subject has been irradiated, and store the generated image data have been put to practical use.

As a radiographic apparatus that acquires, as a digital image, X rays that have been transmitted through a subject in this manner, in Japanese Patent Application Laid-Open Publication (JP-A) No. 2002-204794, there is disclosed an apparatus that controls the movement of a tube that outputs radiation depending on the type of apparatus that generates radiation and the aperture of an irradiation field.

In JP-A No. 2005-198975, there is disclosed a technology that reduces halation on an image caused by a mechanical shift in an X-ray irradiation field aperture or the like.

As a technology that manages radiation amounts, in JP-A No. 2007-181686, there is disclosed a technology that creates patient radiation amount measurement information on the basis of radiation amount measurement data of radiation to which a patient has been exposed.

In JP-A No. 2004-201757, there is disclosed a technology that determines, by calculation, amounts of X rays with which an examinee has been irradiated and stores and manages the cumulative value of the X-ray amounts.

SUMMARY OF THE INVENTION

The present invention has been made in view of the above circumstances and provides a radiographic apparatus and a radiographic method.

According to an aspect of the invention, there is provided a radiographic apparatus including: an irradiation unit that irradiates a subject with radiation; an aperture that regulates an irradiation range of the radiation with which the subject is to be irradiated from the irradiation unit; an aperture controller that controls an opening area of the aperture; an irradiation area calculation unit that calculates an irradiation area of the irradiation range on the basis of the opening area of the aperture; and a controller that controls the irradiation of the subject with the radiation by the irradiation unit on the basis of a comparison result between the irradiation area and a detection area of the radiation of an image data generator that detects the radiation that has been transmitted through the subject and generates image data.

According to another aspect of the invention, there is provided a radiographic method including: irradiating a subject with radiation; controlling an opening area of an aperture that regulates an irradiation range of the radiation with which the subject is to be irradiated; calculating an irradiation area of the irradiation range on the basis of the opening area of the aperture; and controlling the irradiation of the subject with the radiation on the basis of a comparison result between the irradiation area and a detection area of the radiation of an image data generator that detects the radiation that has been transmitted through the subject and generates image data.

BRIEF DESCRIPTION OF THE DRAWINGS

A preferred embodiment of the present invention will be described in detail based on the following figures, wherein.

DETAILED DESCRIPTION OF THE INVENTION

When radiation is used to photograph a patient, it is necessary to keep the amount of that radiation to a minimum. However, with conventional radiographic apparatus, there is the fear that the patient will end up being exposed to additional radiation when the aperture of the radiation is not appropriately opened.

The present invention has been made in view of the above circumstances and provides a radiographic apparatus and a radiographic method that can prevent a situation where a patient ends up being exposed to additional radiation.

Below, an embodiment of the present invention will be described in detail with reference to the drawings.

Figure 1:
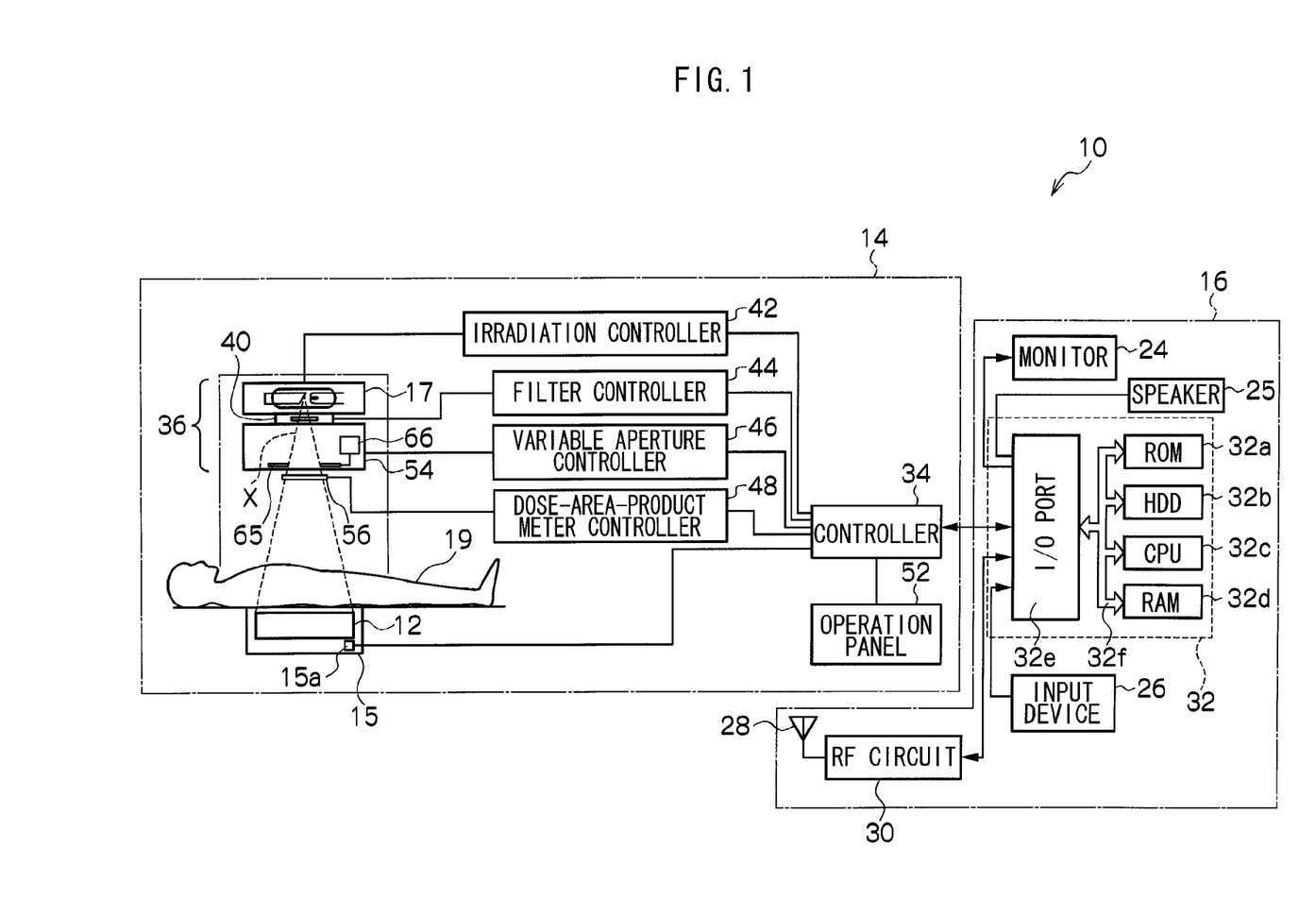
FIG. 1 is a diagram showing the general configuration of a radiographic image detection system pertaining to the embodiment.

As shown in FIG. 1, a radiographic image detection system 10 pertaining to the present embodiment is equipped with an electronic cassette 12, a radiographic apparatus 14 and a console 16. The electronic cassette 12 is portable and is capable, each time it is irradiated with radiation that carries image information, of converting the image information into image data, storing the image data and wirelessly transmitting the image data.

Figure 2A:
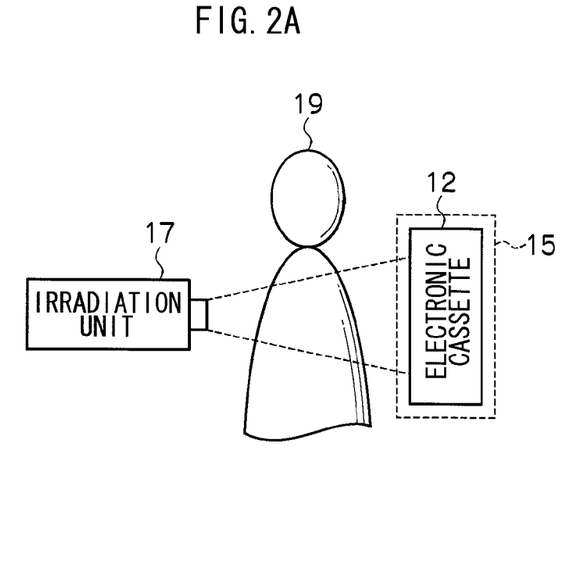
FIG. 2A is a general diagram showing the disposition of an electronic cassette during radiographic image photographing.

As shown in FIG. 2A, the electronic cassette 12 is loaded into a cassette loading unit 15 of the radiographic apparatus 14 during photographing of a radiographic image, whereby the electronic cassette 12 is disposed a distance away from an irradiation unit 17 that irradiates a subject 19 with radiation such as X rays. Between the irradiation unit 17 and the electronic cassette 12 is a photographing position for the subject 19 to be positioned in. When photographing of a radiographic image is instructed, the irradiation unit 17 emits radiation of a radiation amount corresponding to photographing conditions or the like that have been given beforehand. The radiation that has been emitted from the irradiation unit 17 carries image information as a result of being transmitted through the subject 19 positioned in the photographing position, and thereafter the electronic cassette 12 is irradiated with the radiation. Note that the term "photographing" or "photography" as used herein, includes electronic image capture by electrical devices such as radiation detectors and CCDs.

Figure 2B:
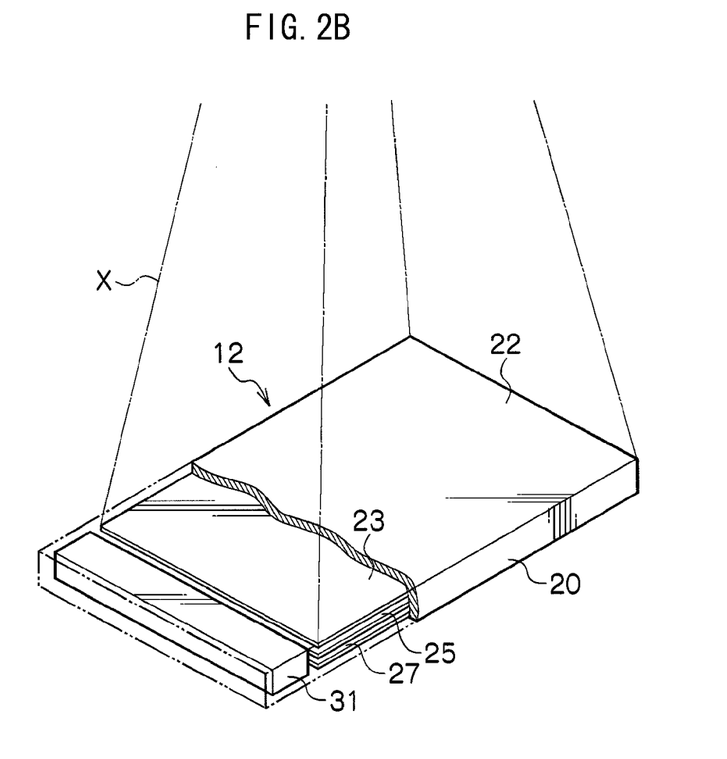
FIG. 2B is a perspective diagram showing the internal configuration of the electronic cassette.

As shown in FIG. 2B, the electronic cassette 12 is covered by a thick, rectangular, flat plate-shaped casing 20 that comprises a material that allows radiation X to be transmitted therethrough. Inside the casing 20, there are disposed, in order from an irradiated surface 22 side of the casing 20 that is irradiated with the radiation X, a grid 23 that removes scattered radiation of the radiation X that arises in accompaniment with the radiation X being transmitted through the subject 19, a radiation detector (radiation detection panel) 25 that detects the radiation X, and a lead plate 27 that absorbs back scattered radiation of the radiation X.

The irradiated surface 22 of the casing 20 may also be configured by the grid 23. A case 31 that houses various circuits (described later) including a microcomputer is disposed on one end side of the inside of the casing 20. It is desirable for a lead plate or the like to be disposed on the irradiated surface 22 side of the case 31 in order to avoid a situation where the various circuits housed inside the case 31 sustain damage in accompaniment with irradiation with the radiation X.

Figure 3:
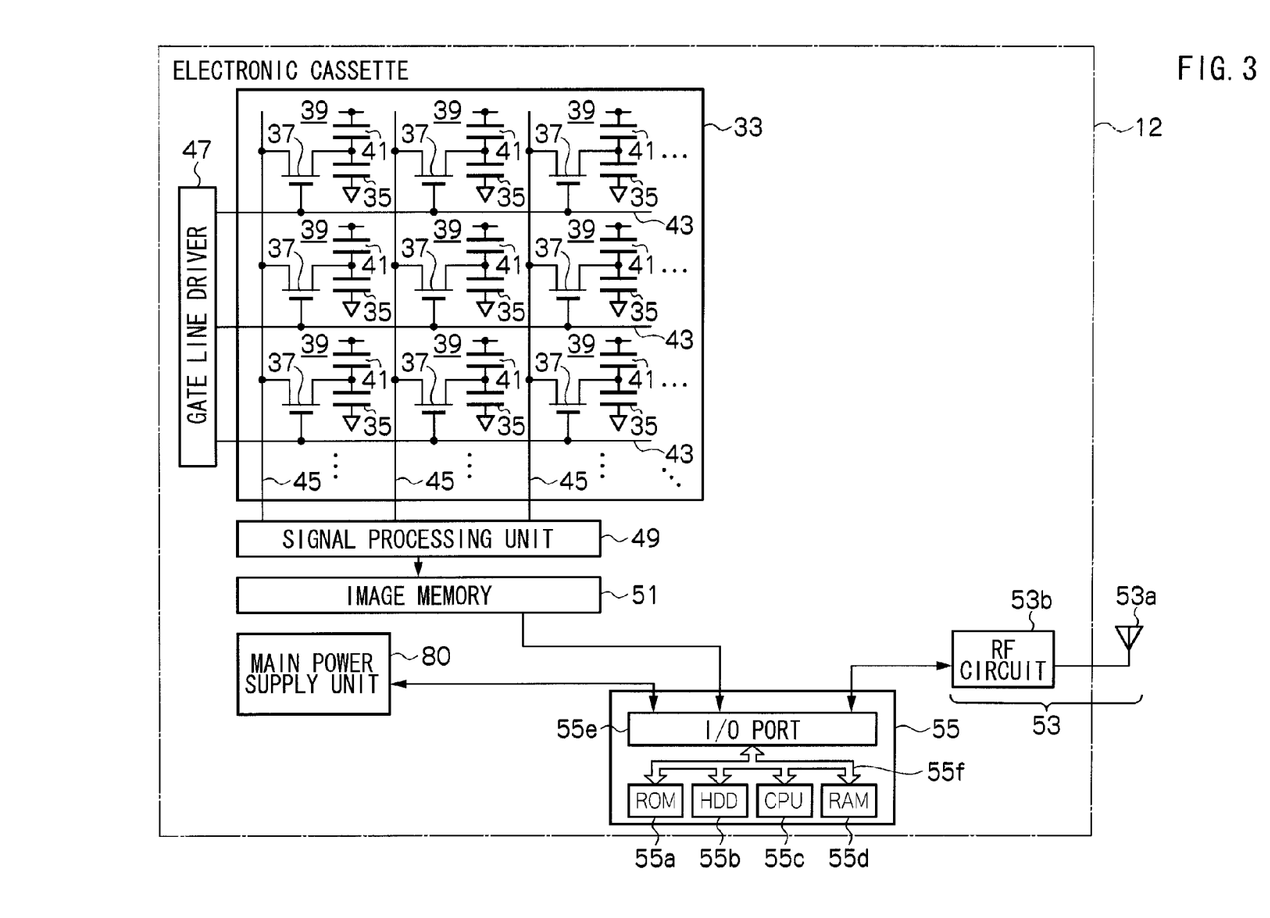
FIG. 3 is a diagram showing the general configuration of the electronic cassette pertaining to the embodiment.

The radiation detector 25 of the electronic cassette 12 is configured as a result of a photoelectric conversion layer that absorbs and converts the radiation X into electric charges being layered on a TFT active matrix substrate 33 shown in FIG. 3. The photoelectric conversion layer comprises, for example, an amorphous selenium (a-Se) whose main component (e.g., having a content percentage equal to or greater than 50%) is selenium, and when the photoelectric conversion layer is irradiated with the radiation X, the photoelectric conversion layer converts the radiation X with which it has been irradiated into electric charges by generating, inside of itself, electric charges (electron-hole pairs) of an electric charge amount corresponding to the amount of the radiation X with which it has been irradiated. The radiation detector 25 may, instead of a radiation-electric charge conversion material such as amorphous selenium that directly converts the radiation X into electric charges, use a fluorescent material and a photoelectric conversion element (photodiode) to indirectly convert the radiation X into electric charges. As the fluorescent material, gadolinium oxysulfide (GOS) and cesium iodide (CsI) are well known. In this case, conversion of the radiation X into light is performed by the fluorescent material, and conversion of the light into electric charges is performed by the photodiode of the photoelectric conversion element.

On the TFT active matrix substrate 33, numerous pixel components 39 (in FIG. 3, the photoelectric conversion layer corresponding to the individual pixel components 39 is schematically shown as photoelectric conversion components 41) equipped with storage capacitors 35 that store the electric charges that have been generated by an electric charge generation layer and TFTs 37 for reading the electric charges that have been stored in the storage capacitors 35 are disposed in a matrix. The electric charges that have been generated by the electric charge generation layer in accompaniment with the irradiation of the electronic cassette 12 with the radiation X are stored in the storage capacitors 35 of the individual pixel components 39. Thus, the image information that had been carried in the radiation X with which the electronic cassette 12 has been irradiated is converted into electric charge information and is held in the radiation detector 25.

On the TFT active matrix substrate 33, there are disposed plural gate lines 43, which extend in a given direction (row direction) and are for switching ON and OFF the TFTs 37 of the individual pixel components 39, and plural data lines 45, which extend in a direction (column direction) orthogonal to the gate lines 43 and are for reading the stored electric charges from the storage capacitors 35 via the TFTs 37 that have been switched ON. The individual gate lines 43 are attached to a gate line driver 47, and the individual data lines 45 are attached to a signal processing unit 49.

When the electric charges are stored in the storage capacitors 35 of the individual pixel components 39, the TFTs 37 of the individual pixel components 39 are switched ON in order in row units by signals that are supplied via the gate lines 43 from the gate line driver 47, and the electric charges that are stored in the storage capacitors 35 of the pixel components 39 whose TFTs 37 have been switched ON are transmitted through the data lines 45 as electric charge signals and are inputted to the signal processing unit 49. Consequently, the electric charges that are stored in the storage capacitors 35 of the individual pixel components 39 are read in order in row units.

The signal processing unit 49 is equipped with amplifiers and sample/hold circuits (not shown) that are disposed for each of the individual data lines 45. The electric charge signals that have been transmitted through the individual data lines 45 are amplified by the amplifiers and are thereafter held in the sample/hold circuits. Multiplexers and A/D converters are attached in order to output sides of the sample/hold circuits (not shown). The electric charge signals held in the individual sample/hold circuits are inputted in order (serially) to the multiplexers and are converted into digital image data by the A/D converters.

An image memory 51 is connected to the signal processing unit 49. The image data that have been outputted from the A/D converters of the signal processing unit 49 are stored in order in the image memory 51. The image memory 51 has a storage capacity that is capable of storing image data of plural frames. Each time photographing of a radiographic image is performed, the image data obtained by the photographing are sequentially stored in the image memory 51.

The electronic cassette 12 is equipped with a communication unit 53, which is for transmitting data to and receiving data from the console 16 by wireless communication, and a controller 55.

The communication unit 53 is equipped with an antenna 53a, which is for transmitting and receiving wireless radio waves, and a radio frequency (RF) circuit 53b. The RF circuit 53b includes a transceiver circuit that transmits and receives data in a predetermined frequency band. The RF circuit 53b performs processing (so-called reception processing) that amplifies, converts the frequency of, and demodulates wireless radio wave signals received via the antenna 53a and outputs the signals to the controller 55 and processing (so-called transmission processing) that modulates, converts the frequency of, and amplifies data inputted from the controller 55 and outputs the data as wireless radio waves via the antenna 53a, to thereby perform wireless communication processing.

The controller 55 is equipped with a read-only memory (ROM) 55a, a hard disk drive (HDD) 55b, a central processing unit (CPU) 55c, a random access memory (RAM) 55d and an input/output (I/O) port 55e. The ROM 55a, the HDD 55b, the CPU 55c, the RAM 55d and the I/O port 55e are interconnected by a bus 55f.

A basic program such as an operating system (OS) and programs for executing various processing are stored in the ROM 55a that serves as a storage medium.

A program for executing a processing routine of image data transmission processing whose details will be described below is stored in the HDD 55b that serves as a storage medium.

The CPU 55c reads and executes the programs from the ROM 55a and the HDD 55b.

Various data are temporarily stored in the RAM 55d.

The image memory 51, the RF circuit 53b and other various circuits and elements are connected to the I/O port 55e.

A power supply unit 80 that supplies power to the various circuits and elements in order to allow the electronic cassette 12 to operate is further disposed in the electronic cassette 12. The power supply unit 80 is connected to the I/O port 55e, and the amount of power that is supplied by the power supply unit 80 to the various circuits and elements is controlled by the control of the controller 55. As the power supply unit 80, a configuration that has a built-in battery (a rechargeable secondary battery) and supplies power to the various circuits and elements from the charged battery is preferable so as to not impair the portability of the electronic cassette 12. However, the power supply unit 80 may also use a primary battery as the battery, or the power supply unit 80 may also have a configuration where it is always attached to a commercial power supply, rectifies and transforms power that has been supplied from the commercial power supply, and supplies the power to the various circuits and elements.

The console 16 is equipped with a monitor 24 (corresponding to a warning unit), a speaker 25 (corresponding to a warning unit), an input device 26 for receiving user instructions and the like, an antenna 28 for transmitting and receiving wireless radio waves, a radio frequency (RF) circuit 30 and a console control device 32.

The monitor 24 is configured to include a liquid crystal display (LCD) that displays images based on inputted information.

The speaker 25 outputs audio and beep sounds based on inputted audio information.

The input device 26 is configured by a keyboard and a mouse and receives user instructions and the like as a result of a user operating the keyboard and the mouse.

The RF circuit 30 includes a transceiver circuit that transmits and receives data in a predetermined frequency band. The RF circuit 30 performs processing (so-called reception processing) that amplifies, converts the frequency of, and demodulates wireless radio wave signals received via the antenna 28 and outputs the signals to the console control device 32 and processing (so-called transmission processing) that modulates, converts the frequency of, and amplifies data inputted from the console control device 32 and outputs the data as wireless radio waves via the antenna 28, to thereby perform wireless communication processing.

The console control device 32 is equipped with a read-only memory (ROM) 32a, a hard disk drive (HDD) 32b (corresponding to a storage unit), a central processing unit (CPU) 32c, a random access memory (RAM) 32d and an input/output (I/O) port 32e. The ROM 32a, the HDD 32b, the CPU 32c, the RAM 32d and the I/O port 32e are interconnected by a bus 32f.

A basic program such as an operating system (OS) is stored in the ROM 32a that serves as a storage medium.

Programs for executing processing routines such as X-ray irradiation processing whose details will be described below are stored in the HDD 32b that serves as a storage medium.

The CPU 32c reads and executes the programs from the ROM 32a and the HDD 32b.

Various data are temporarily stored in the RAM 32d.

The monitor 24, the input device 26 and the RF circuit 30 are connected to the I/O port 32e. Further, the radiographic apparatus 14 is connected to the I/O port 32e.

The radiographic apparatus 14 is equipped with a controller 34 (corresponding to an irradiation area calculation unit, a controller, a region information input unit, a radiation amount calculation unit and a subject information input unit), an irradiation system 36 that irradiates the subject 19 with radiation (in the present embodiment, X rays), the cassette loading unit 15, an irradiation controller 42, a filter controller 44, a variable aperture controller 46, a dose-area-product meter controller 48 and an operation panel 52.

The irradiation system 36 is equipped with an irradiation unit 17 that irradiates the subject 19 with X rays as radiation, a filter 40 that hardens the beams of the radiated X rays, a variable aperture device 54 that controls the output range of the X rays and a dose-area-product meter 56 (corresponding to a radiation amount detection unit).

The irradiation unit 17 generates the X rays when a high voltage is applied thereto from a high voltage generator (not shown). The operation of generating the X rays is controlled by the irradiation controller 42 and the controller 34.

The filter 40 is configured such that it can be freely replaced by inserting and withdrawing a filter made of various metal plates or the like in order to obtain beam hardening corresponding to the purpose of examination or the characteristic of the region of the subject 19 that is to be photographed. Replacement or the like of the filter 40 is driven and controlled by the filter controller 44.

The variable aperture device 54 is configured to include an aperture 65 that comprises plural aperture blades and a blade drive unit 66 that variably sets the aperture 65 to be wide or narrow. The variable aperture device 54 is connected to the variable aperture controller 46.

The aperture blades that configure the aperture 65 comprise an X-ray shielding material and are movably disposed. By adjusting the arranged relationship of the plural aperture blades on the basis of the control of the variable aperture controller 46 via the controller 34 depending on input instructions from the operation panel 52 or photographing conditions that have been inputted from the console 16, for example, the desired opening is obtained. Thus, the above-described X-ray irradiation field X can be obtained.

The dose-area-product meter 56 measures the radiation amount of the X rays that have passed through the aperture 65. The dose-area-product meter 56 is controlled by the dose-area-product meter controller 48.

The X rays are first emitted from an X-ray window in the irradiation unit 17, pass through the filter 40 that hardens the beams of the X rays, pass through the variable aperture device 54 for narrowing the X-ray irradiation field X to a necessary minimum to promote exposure amount reduction, and pass through the dose-area-product meter 56, whereby the subject 19 is irradiated with the X rays. Then, the electronic cassette 12 that has been loaded into the cassette loading unit 15 is irradiated with the X rays that have been transmitted through the subject 19, and image data representing an image corresponding to the radiation amount of the radiation that has been transmitted through the subject 19 are generated in the electronic cassette 12.

The cassette loading unit 15, into which the electronic cassette 12 is loadable and which is disposed such that the electronic cassette 12 is irradiated with the radiation that has been emitted from the irradiation system 36 and transmitted through the subject 19 when the electronic cassette 12 has been loaded into the cassette loading unit 15, is disposed in the radiographic apparatus 14. A sensor 15a that outputs a signal (e.g., an ON signal) indicating that the electronic cassette 12 is loaded into the cassette loading unit 15 when the electronic cassette 12 has been loaded into the cassette loading unit 15 and outputs a signal (e.g., an OFF signal) indicating that the electronic cassette 12 is not loaded into the cassette loading unit 15 when the electronic cassette 12 has not been loaded into the cassette loading unit 15 is disposed in the cassette loading unit 15. The sensor 15a is connected to the controller 34.

The controller 34 is configured by a microcomputer including a ROM (not shown) that serves as a storage medium in which are stored a basic program such as an operating system (OS), a program for executing a processing routine of radiographic processing whose details will be described below and programs for executing processing routines of various processing, a CPU (not shown) that controls the radiographic apparatus 14 by reading and executing the programs from the ROM, a RAM (not shown) that temporarily stores various data, an I/O port (not shown) and a memory that serves as a storage unit in which various information is stored. The controller 34 is connected to the console 16 and controls the radiographic apparatus 14.

Figure 4:
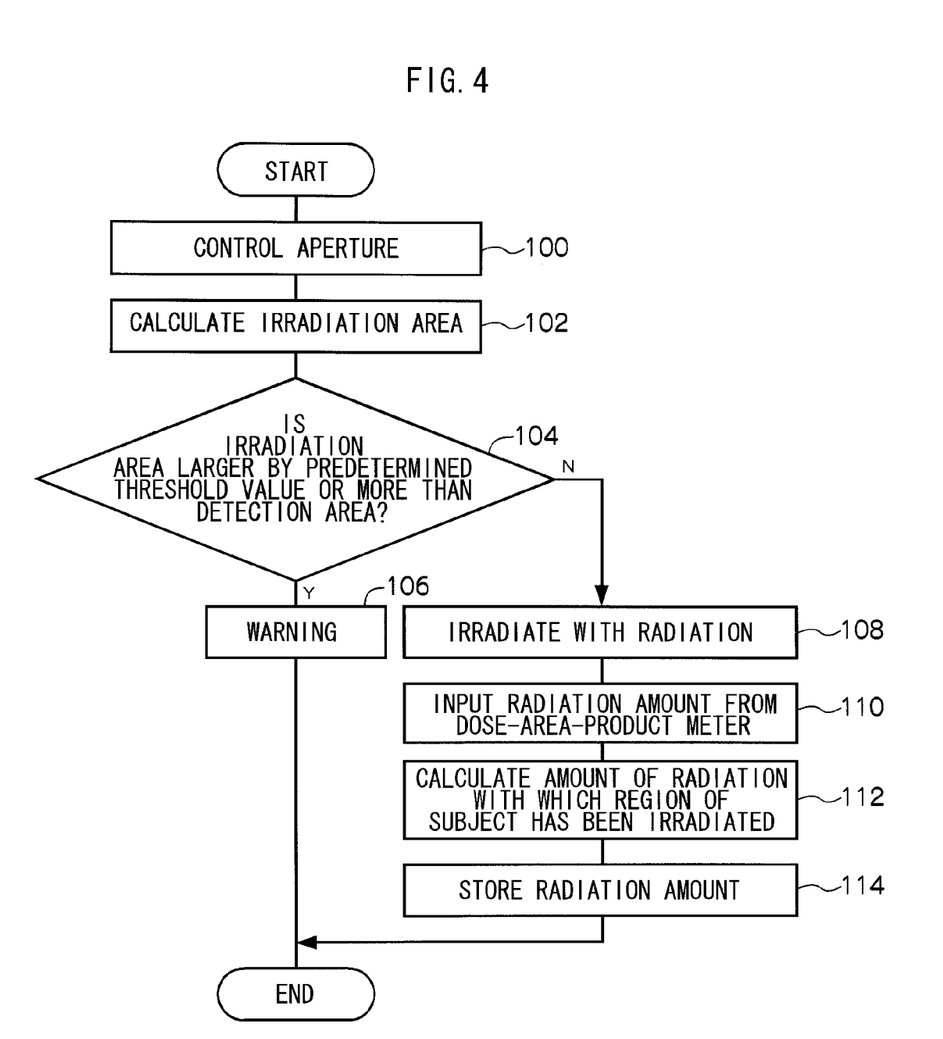
FIG. 4 is a diagram showing a flowchart of a processing routine of radiographic processing that a controller of a radiographic apparatus pertaining to the embodiment executes.

Next, a processing routine of X-ray irradiation processing that the controller 34 of the radiographic apparatus 14 executes will be described with reference to FIG. 4. In the present embodiment, the X-ray irradiation processing is executed when photographing conditions (e.g., subject information relating to the subject, the region, angle and number of exposures of photography, tube voltage, tube current and irradiation time for irradiating the subject 19 with the radiation X, a detection area of the radiation of the electronic cassette 12, and sensitivity, etc.) of a radiographic image have been inputted from the input device 26 of the console 16, photographing has been instructed, and the photographing conditions have been inputted to the controller 34 via the console control device 32.

In step 100, the controller 34 instructs the variable aperture controller 46 to control the aperture 65 such that the aperture 65 opens in the desired opening, i.e., the desired opening area, corresponding to the photographing conditions such as, for example, the region of photography. Thus, the aperture 65 is controlled so as to become the desired opening area by the variable aperture controller 46. In the present embodiment, as one example, the opening of the aperture 65 is set such that an irradiation range of the radiation with which the subject 19 is to be irradiated substantially coincides with a detection range of the radiation of the electronic cassette 12.

In step 102, the controller 34 calculates an irradiation area Sa of the radiation X with which the subject 19 is to be irradiated. The irradiation area Sa can be determined by a predetermined arithmetic expression whose parameters are, for example, an opening area A of the aperture 65 and a magnifying power B that has been determined in response to a distance d between the irradiation unit 17 and the electronic cassette 12.

In step 104, the controller 34 judges whether or not the irradiation area Sa that has been calculated in step 102 is larger by a predetermined threshold value or more in comparison to a detection area Sb of the radiation of the electronic cassette 12 that has been inputted as a photographing condition. The predetermined threshold value is set to a value with which the controller 34 can judge, when the irradiation area Sa is larger by this predetermined value or more than the detection area Sb, that the radiation amount of the radiation with which the subject 19 is to be irradiated exceeds an allowable range that has been determined beforehand.

When the irradiation area Sa is larger by the predetermined threshold value or more than the detection area Sb, the controller 34 moves to step 106, and when the irradiation area Sa is not larger by the predetermined threshold value or more than the detection area Sb, the controller 34 moves to step 108.

In step 106, the controller 34 instructs the irradiation controller 42 to prohibit the subject 19 from being irradiated with the radiation and performs predetermined warning processing.

Examples of the warning processing may include processing where the controller 34 instructs the console 16 to display a warning message indicating that, for example, the irradiation area is too large, that is, that the amount of radiation with which the subject 19 is to be irradiated is too large. Thus, a warning message is displayed on the monitor 24 of the console 16, and an operator can be prompted to change the photographing conditions such as the opening of the aperture 65.

The warning processing may also be configured such that the controller 34 instructs the console 16 to output a warning message or a warning sound indicating that the amount of radiation with which the subject 19 is to be irradiated is too large. Thus, a warning message is outputted as audio, or a warning sound such as a beep sound is outputted, from the speaker 25 of the console 16.

The warning may be configured such that an operator such as a technician can stop the warning by operating the input device 26 or the operation panel 52.

When the irradiation area Sa is not larger by the predetermined threshold value or more than the detection area Sb, then in step 108, the controller 34 instructs the irradiation controller 42 such that the radiation is outputted. Thus, the irradiation controller 42 controls the irradiation unit 17, and the radiation is outputted. The outputted radiation has its irradiation range narrowed by the aperture 65 and is transmitted through the dose-area-product meter 56, and the subject 19 is irradiated with that radiation.

The radiation that has been transmitted through the subject 19 is converted into image data by the electronic cassette 12, and the image data outputted to the console 16 by wireless communication. The console 16 displays the received image data on the monitor 24, for example, and stores the received image data in the HDD 32b.

In step 110, the controller 34 inputs, via the dose-area-product meter controller 48, the radiation amount that has been measured by the dose-area-product meter 56. The radiation amount is inversely proportional to the square of the distance of the radiation source that outputs the radiation. Consequently, the controller 34 determines the radiation amount in the position of the subject 19 on the basis of the radiation amount that has been measured by the dose-area-product meter 56 and the distance between the irradiation unit 17 and the subject 19.

In step 112, the controller 34 inputs the image data generated by the electronic cassette 12 from the console 16 and calculates, on the basis of the image data, the radiation amount in the position of the subject 19 determined in step 110 and the photographing region inputted as a photographing condition, the amount of radiation with which the subject 19 has actually been irradiated.

Specifically, for example, when the photographing region is a large photographing region, such as an abdomen, having a large area that is equal to or greater than the detection area of the radiation of the electronic cassette 12, then the subject 19 is irradiated with the entire radiation amount determined in step 110.

When the photographing region is a small photographing region, such as an arm, having a smaller area than the detection area of the radiation of the electronic cassette 12, first, the controller 34 calculates, on the basis of the image generated by the electronic cassette 12, the area of a portion (also called a "through portion" below) where the electronic cassette 12 has been directly irradiated with the radiation without that radiation being transmitted through the subject 19. The controller 34 can determine the area of the through portion by, for example, setting beforehand a numerical range of image data when the electronic cassette 12 has been directly irradiated with the radiation and judging whether or not the image data belong to this numerical range.

Then, the controller 34 determines the ratio of the area of the through portion with respect to the detection area of the radiation of the electronic cassette 12 and multiplies the radiation amount in the position of the subject 19 determined in step 110 by this ratio. Thus, the amount of radiation with which the arm of the subject 19 has actually been irradiated can be calculated.

In step 114, the controller 34 outputs the radiation amount determined in step 112 to the console 16 together with the subject information that has been inputted as a photographing condition. Thus, the console 16 stores, in the HDD 32b, the inputted radiation amount in association with the subject information. When a radiation amount of the same subject has been inputted, the console 16 adds the inputted radiation amount to the radiation amount that has been associated with that subject and stores it. Thus, how much radiation the same subject has been irradiated with in the past can be easily understood.

In the present embodiment, a case has been described where the controller 34 moves to step 108 and irradiates the subject 19 with the radiation when it has been judged in step 104 that the irradiation area is not larger by the predetermined threshold value or more than the detection area. However, the controller 34 may also be configured such that, even when it has been judged that the irradiation area is not larger by the predetermined threshold value or more than the detection area, such as, for example, when the orientation of the electronic cassette 12 has not been set in an appropriate orientation with respect to the photographing region that has been set in the photographing conditions, the controller 34 warns when a state that is different from the photographing conditions has been detected.

In the present embodiment, a case has been described where the electronic cassette was used as an example of a radiographic image detection device, but the radiographic image detection device is not limited to this. The present invention is applicable also to a computed radiography (CR) system that uses an imaging plate or a portable system such as film, and the present invention is applicable also to a built-in system where a CR or a digital radiography (DR) detector is built into the apparatus.

According to a first aspect of the invention, there is provided a radiographic apparatus including: an irradiation unit that irradiates a subject with radiation; an aperture that regulates an irradiation range of the radiation with which the subject is to be irradiated from the irradiation unit; an aperture controller that controls an opening area of the aperture; an irradiation area calculation unit that calculates an irradiation area of the irradiation range on the basis of the opening area of the aperture; and a controller that controls the irradiation of the subject with the radiation by the irradiation unit on the basis of a comparison result between the irradiation area and a detection area of the radiation of an image data generator that detects the radiation that has been transmitted through the subject and generates image data.

According to the first aspect, the controller controls the irradiation of the subject with the radiation by the irradiation unit on the basis of the comparison result between the irradiation area of the radiation to the subject that has been calculated by the irradiation area calculation unit and the detection area of the radiation of the image data generator that detects the radiation that has been transmitted through the subject and generates image data. Thus, a situation where a patient ends up being exposed to additional radiation can be prevented.

According to a second aspect of the invention, in the first aspect, the controller may prohibit the irradiation of the subject with the radiation by the irradiation unit when the irradiation area is larger by a predetermined threshold value or more than the detection area.

According to a third aspect of the invention, in the first aspect, the radiographic apparatus may further include a warning unit that warns when the irradiation area is larger by a predetermined threshold value or more than the detection area.

According to a fourth aspect of the invention, in the third aspect, the warning unit may include at least one of a display unit that displays a warning message indicating that the irradiation area is larger by the predetermined threshold value or more than the detection area and a warning sound output unit that outputs a warning sound indicating that the irradiation area is larger by the predetermined threshold value or more than the detection area.

According to a fifth aspect of the invention, in the first aspect, the radiographic apparatus may further include a radiation amount detection unit that detects the radiation amount of the radiation that has passed through the aperture, a region information input unit that inputs region information relating to a region of the subject that is to be irradiated with the radiation, and a radiation amount calculation unit that calculates the amount of the radiation with which the subject has been irradiated on the basis of the radiation amount detected by the radiation amount detection unit, the region information inputted by the region information input unit and the image data generated by the image data generator.

Thus, the radiation amount of the radiation with which the subject has actually been irradiated can be more accurately calculated.

According to a sixth aspect of the invention, in the fifth aspect, the radiographic apparatus may further include a subject information input unit that inputs subject information relating to the subject, wherein the controller may store, in a storage unit, the radiation amount calculated by the radiation amount calculation unit in association with the subject information.

According to a seventh aspect of the invention, in the sixth aspect, the controller may add the radiation amount calculated by the radiation amount calculation unit to a past radiation amount stored in the storage unit and store, in the storage unit, that radiation amount in association with the subject information.

Thus, the cumulative total of past radiation amounts can be easily understood per subject.

According to an eighth aspect of the invention, there is provided a radiographic method including: irradiating a subject with radiation; controlling an opening area of an aperture that regulates an irradiation range of the radiation with which the subject is to be irradiated; calculating an irradiation area of the irradiation range on the basis of the opening area of the aperture; and controlling the irradiation of the subject with the radiation on the basis of a comparison result between the irradiation area and a detection area of the radiation of an image data generator that detects the radiation that has been transmitted through the subject and generates image data.

According to the eighth aspect, the irradiation of the subject with the radiation is controlled on the basis of the comparison result between the irradiation area of the radiation to the subject that has been calculated and the detection area of the radiation of the image data generator that detects the radiation that has been transmitted through the subject and generates image data. Thus, a situation where a patient ends up being exposed to additional radiation can be prevented.

As described above, according to the present invention, a situation where a patient ends up being exposed to additional radiation can be prevented.

Embodiments of the present invention are described above, but the present invention is not limited to the embodiments as will be clear to those skilled in the art.

What is claimed is:

1. A radiographic apparatus comprising:
   an irradiation unit that irradiates a subject with radiation;
   an image data generator, configured to detect radiation over a detection area, which detects radiation that has been transmitted through the subject, and which generates corresponding image data;
   an aperture that regulates an irradiation range of the radiation with which the subject is to be irradiated from the irradiation unit;
   an aperture controller that controls an opening area of the aperture;
   an irradiation area calculation unit that calculates an irradiation area of the irradiation range on the basis of the opening area of the aperture;
   a controller that controls the irradiation of the subject with the radiation by the irradiation unit on the basis of a comparison result between the irradiation area and the detection area;
   a radiation amount detection unit that detects an amount of the radiation that has passed through the aperture;
   a region information input unit that inputs region information relating to a region of the subject that is to be irradiated with the radiation; and
   a radiation amount calculation unit that calculates an amount of the radiation with which the subject has been irradiated on the basis of the radiation amount detected by the radiation amount detection unit, the region information inputted by the region information input unit and the image data generated by the image data generator.

2. The radiographic apparatus according to claim 1, wherein the controller prohibits the irradiation of the subject with the radiation by the irradiation unit when the irradiation area is larger by a predetermined threshold value or more than the detection area.

3. The radiographic apparatus according to claim 1, further comprising a warning unit that warns when the irradiation area is larger by a predetermined threshold value or more than the detection area.

4. The radiographic apparatus according to claim 3, wherein the warning unit includes a display unit that displays a warning message indicating that the irradiation area is larger by the predetermined threshold value or more than the detection area, a warning sound output unit that outputs a warning sound indicating that the irradiation area is larger by the predetermined threshold value or more than the detection area, or a combination thereof.

5. The radiographic apparatus according to claim 1, further comprising a subject information input unit that inputs subject information relating to the subject, wherein the controller stores, in a storage unit, the radiation amount calculated by the radiation amount calculation unit in association with the subject information.

6. The radiographic apparatus according to claim 5, wherein the controller adds the radiation amount calculated by the radiation amount calculation unit to a past radiation amount stored in the storage unit and stores a total radiation amount, in the storage unit, in association with the subject information.

7. The radiographic apparatus according to claim 6, wherein when the region is a region having an area equal to or greater than the detection area, the radiation amount calculation unit calculates the detected radiation amount as being the radiation amount, and, when the region is a region having an area smaller than the detection area, the radiation amount calculation unit calculates the radiation amount using a ratio, with respect to the detection area, of an area of a portion where the image data generator has been irradiated with the radiation without that radiation being transmitted through the subject.

8. The radiographic apparatus according to claim 1, wherein the image data generator includes an electronic cassette.

9. A radiographic method comprising:
   irradiating a subject with radiation;
   detecting, over a detection area of an image data generator, radiation transmitted through the subject, and generating image data corresponding thereto;
   controlling an opening area of an aperture that regulates an irradiation range of the radiation with which the subject is to be irradiated;
   calculating an irradiation area of the irradiation range on the basis of the opening area of the aperture;
   controlling the irradiation of the subject with the radiation on the basis of a comparison result between the irradiation area and the detection area;
   detecting an amount of the radiation that has passed through the aperture;
   inputting region information relating to a region of the subject that is to be irradiated with the radiation; and
   calculating an amount of the radiation with which the subject has been irradiated on the basis of the detected radiation amount, the region information and the image data.

* * * * *